United States Patent
Arndt

(10) Patent No.: US 6,749,919 B2
(45) Date of Patent: Jun. 15, 2004

(54) INKLESS FINGERPRINT COMPOSITION AND APPLICATOR THEREFOR

(75) Inventor: Douglas C. Arndt, Ventura, CA (US)

(73) Assignee: Armor Holdings Forensics Inc., Jacksonville, FL (US)

( * ) Notice: Subject to any disclaimer, the term of this patent is extended or adjusted under 35 U.S.C. 154(b) by 226 days.

(21) Appl. No.: 10/021,212

(22) Filed: Oct. 26, 2001

(65) Prior Publication Data

US 2003/0083199 A1 May 1, 2003

(51) Int. Cl.⁷ ............................................. A61B 5/117
(52) U.S. Cl. .................. 428/101; 428/189; 428/192; 428/195.1; 428/201; 427/1; 427/256
(58) Field of Search ...................... 427/1, 256; 428/101, 428/189, 192, 195.1, 201

(56) References Cited

U.S. PATENT DOCUMENTS

| | | | |
|---|---|---|---|
| 3,089,459 A | * 5/1963 | Picard | 118/31.5 |
| 4,029,012 A | 6/1977 | Smith, III et al. | |
| 4,182,261 A | 1/1980 | Smith, III et al. | |
| 4,363,286 A | * 12/1982 | Leavitt et al. | 118/31.5 |
| 4,427,111 A | 1/1984 | Laipply | |
| 4,427,115 A | 1/1984 | Laipply | |
| 4,696,393 A | 9/1987 | Laipply | |
| 4,699,077 A | 10/1987 | Meadows et al. | |
| 4,983,415 A | 1/1991 | Arndt et al. | |
| 5,046,608 A | 9/1991 | Laipply | |
| 5,078,426 A | * 1/1992 | Reardon | 283/78 |
| 5,143,551 A | * 9/1992 | Mason et al. | 118/31.5 |
| 5,263,742 A | * 11/1993 | Koch | 283/78 |
| 5,737,071 A | * 4/1998 | Arndt | 356/71 |
| 5,879,453 A | * 3/1999 | Streeter et al. | 118/31.5 |
| 5,919,292 A | * 7/1999 | Arndt | 106/31.03 |
| 6,027,556 A | 2/2000 | Arndt | |
| 6,488,750 B1 | * 12/2002 | Arndt | 106/31.03 |

* cited by examiner

Primary Examiner—Shrive P. Beck
Assistant Examiner—Kirsten Crockford Jolley
(74) Attorney, Agent, or Firm—Harold L. Jackson

(57) ABSTRACT

A nonstaining ink (or inkless) fingerprint composition and applicator comprises two nonpermeable foil strips, made of Mylar, for example, having the same width with one strip being slightly longer than the other. A thin layer or coating of an inkless (or nonstaining) fingerprint composition is sandwiched between the superimposed foil strips leaving a small border including a small area at the end of the strips free of the composition. The inkless composition which includes a color former and may or may not include a developer is in a semisolid state and room temperature and in a liquid state at about 110° F. and above.

21 Claims, 2 Drawing Sheets

INKLESS FINGERPRINT COMPOSITION AND APPLICATOR THEREFOR

FIELD OF THE INVENTION

The present invention relates to a disposable applicator containing a non-staining fingerprint composition and method of making the same.

DESCRIPTION OF THE PRIOR ART

Although there are other methods of identifying individuals, it has become readily apparent that fingerprints provide a relatively simple, unique and absolute means of identification that requires little cooperation from the subject. Since fingerprints are archived they must be permanent and because they are often captured by an electronic camera, the preferred color of fingerprint images is black. Printer's ink, which contains carbon pigmentation, meets the requirements of image permanency and color and has been and is still being widely used. Generally the ink is stored in a convenient reservoir such as a tube (for application to a plate prior to the fingerprinting procedure) or in a pad (against which the person's fingerprint area is pressed before being deposited onto a paper substrate).

The tube and plate system, while skill intensive and time consuming to use, lends itself to large scale fingerprint operations such as police stations etc. The ink pad system, while lending itself to smaller scale fingerprint operations, has disadvantages such as the need to periodically replenish the ink and store replacement ink.

Disposable ink coaters, while eliminating the need to replenish ink in a pad, are generally expensive on a per use basis. For example, see my U.S. Pat. No. 6,027,556 ("'556 patent") which describes an applicator for a nonstaining ink in which an absorbent ink pad material made of a melt-blown calendared polyester fabric is encapsulated between two gas-impermeable sheets, heat sealed along their edges. A spine is provided along one end of the applicator to allow a user to grasp the spine after the sheets are opened and rub the pad across a subject's skin such as his or her foot thereby coating that area with the nonstaining ink.

The least expensive ink coaters are in the form of ink foils. The foils are comprised of two superimposed strips of polyester film with a coating of viscous ink solution disposed between the strips. The ink is composed of carbon black and lanolin. See FIG. 1 of the drawings which illustrates a carbon pigmented ink and lanolin solution 10 deposited on a thin plastic film 12 and FIG. 2 which illustrates the ink sandwiched between the lower film strip 12 and an upper film strip 16. The strips, generally made of Mylar® (Mylar is a registered trademark of E. I. DuPont de Nemours & Company), are of the same length with a margin 14 at one end of each strip on which ink is not deposited during the manufacturing process. The inkless margins 14 are apparently designed to allow a user to separate the two strips. After the layers 12 and 16 of film are peeled apart, one or both of the strips may be placed on a flat surface such as a table or hood of a patrol vehicle with the ink side up so that the ink may be transferred to the subject's fingerprint area in a conventional manner. The user thus has one or both surfaces from which to ink the fingers, palms, feet of a person to be fingerprinted. The tackiness of the ink keeps the strips intact until they are peeled apart by hand. The lanolin, because it has a melting point of about 107 degrees F and a softening point much less than that, is problematic because in warm environments the ink can migrate and impair the quality of the coating as well as leak out from between the strips of film. Typically, this type of carbon pigmented ink stains the skin severely and is difficult to remove because the tackiness needed to keep the coating and film intact also makes the ink adhere strongly to the skin. The typical foils can be hard to open because of the difficulty grasping the separate marginal areas 14 of the foil strips.

There is a need for an inexpensive fingerprint composition and disposable applicator therefore which overcomes the above problems.

SUMMARY OF THE INVENTION

A non-staining or inkless fingerprint composition and disposible applicator therefore, in accordance with the present invention, includes two substantially nonpermeable foil strips having substantially the same width. The strips are superimposed one on one another with one of the strips being slightly longer than the other to provide an extended free pull-tab. The shorter strip also has a free pull-tab which extends under (or over) the extended pull-tabs to physically separate the strips thereby enabling the fingerprint composition on one or both of the strips to be applied to a person's fingertip area. A thin layer of an inkless (or nonstaining) fingerprint composition is sandwiched between the superimposed foil strips leaving a small peripheral border including the area between the extended and shorter pull-tabs free of the composition.

An inkless composition includes a solution of a color former which is semisolid at ambient temperature. The color former is characterized by forming a perceivable colorant product representing a person's fingerprint when applied to the person's fingerprint area and deposited onto a paper substrate in the presence of a developer. The color former may comprise one of the transition metal salts and the solvent may include glycol, glycol fatty acid esters, fatty acids, polyoxyethylene fatty esters or other reagents which are compatible with the color former and are sufficiently heat resistant to maintain the composition in a semisolid state at room temperature, e.g., about 100 ° F. or less. It is to be noted that the developer may be separate from the color former solution or an integral constituent thereof with a sufficient amount of chelating agent to inhibit reaction between the color former and developer until the composition is applied to the fingerprint area and deposited onto the paper substrate.

With respect to the method of making the disposable applicator with the inkless composition therein, I provide two substantially nonpermeable thin film strips of plastic foil approximately the same width with one strip being slightly longer than the other. For example, the strips may be cut from a suitable stock material such as a Mylar® plastic strip having a thickness of 0.001"–0.005" and preferably within the range of 0.002" to 0.003". I also provide an inkless fingerprint composition with the constituents discussed above. The composition is heated to liquify the semisolid composition and then coated on one (or both) of the strips leaving a peripheral margin, including the area under the pull-tabs free of the composition. The strips are then superimposed on one another with the inkless composition sandwiched therebetween and left to cool to room temperature.

The invention may be best understood in reference to the following description taken in conjunction with the accompanying drawings.

DESCRIPTION OF THE PREFERRED EMBODIMENT

Figure 1:
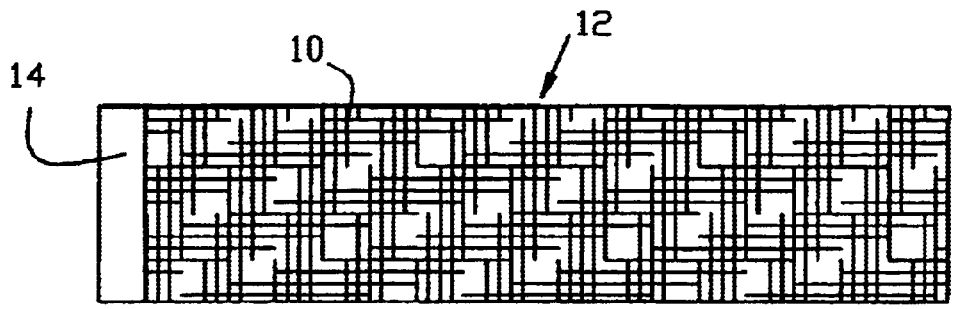
FIG. 1 is a top plan view of the lower foil strip of a disposable prior art fingerprint ink coater with ink coated thereon.
Figure 2:
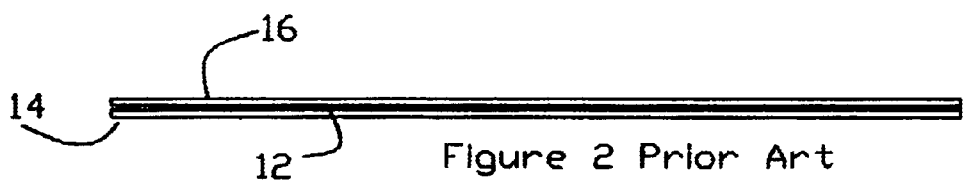
FIG. 2 is a side view of the lower strip of FIG. 1 and a top strip superimposed thereon with the ink sandwiched between the strips.
Figure 3:
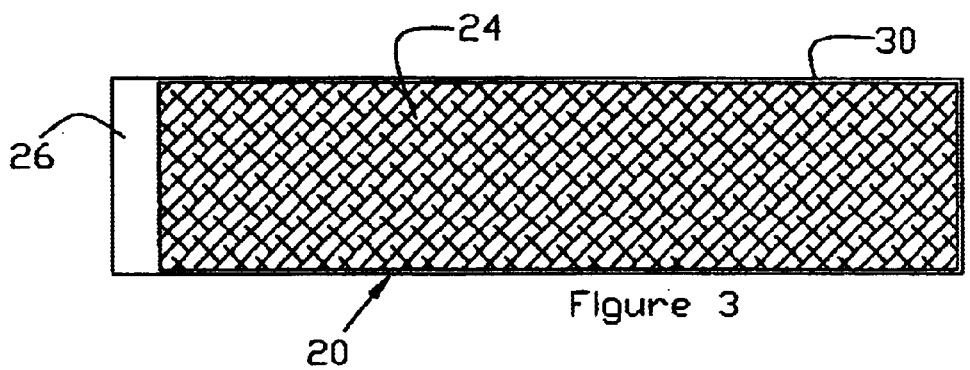
FIG. 3 is a top plan view of a lower foil strip of a disposable coater with a layer of inkless fingerprint composition placed thereon in accordance with the present invention.
Figure 4:
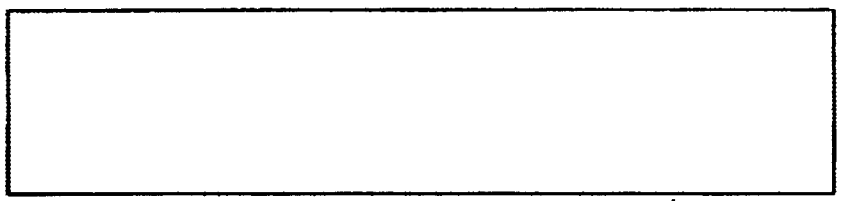
FIG. 4 is a bottom plan view of an upper strip to be overlayed on the lower strip of FIG. 3 without any inkless composition thereon.
Figure 5:
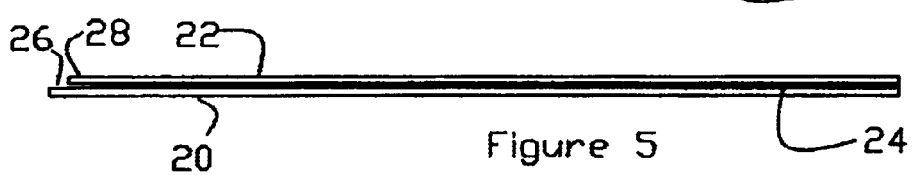
FIG. 5 is a side view of the superimposed strips of FIGS. 3 and 4 with the inkless composition sandwiched therebetween.

Referring now to the drawings and particularly to FIGS. 3, 4, and 5 the preferred embodiment of the present invention includes a pair of substantially nonpermeable plastic foil strips 20 and 22 made, for example, from Mylar with a layer or coating of a nonstaining or inkless fingerprint composition 24 sandwiched therebetween. As is illustrated the strips are of the same width with the bottom strip being slight longer, e.g., ¼ inches, to form an extended free pull-tab 26 which extends beyond the upper strip 22 in the assembled condition. The upper strip also includes a shorter pull-tab 28 so that in the assembled condition a user can grasp both pull-tabs and by applying opposite forces to the tabs separate the two strips. A coating or layer of an inkless fingerprint composition is applied to one or both strips before assembly leaving uncoated only a peripheral border 30 of say about 1/16" in width and the area between the pull-tabs 26 and 28.

The inkless fingerprint composition includes a color former which may be one or more of transition metal salts selected from the groups 5A–8A, 1B–5B and 7B of the periodic Table of Elements. More specifically while salts of iron, e.g., ferric chloride, have also been found to be very satisfactory, salts of titanium, vanadium, chromium, magnesium, cobalt, nickel, copper, zirconium, zinc, niobium, molybdenum, silver, tantalum and tungsten have been found satisfactory.

A suitable solvent for the color may comprise one or more reagents from the following group: glycol, glycol fatty acid esters, fatty acids, and fatty alcohols and more specifically one or more of the following: glyceryl lanolate, glyceryl laurate, glyceryl myristate, glyceryl oleate/palmitate/ricinoleate, polyethylene glycol castor oils/cocoates/isostearates, polyethylene glycol lanolates, stearyl alcohol, myristyl alcohol, cetyl palmitate, cetyl alcohol and bees wax (a blend of fatty acid esters).

The solvent must be compatible with the color former and sufficiently heat resistive to maintain the composition in a semisolid state at room temperature, e.g., about 100° or less and in a liquid phase at about 110° F. to 150° F. and preferably within a temperature range of 115° F. to 130° F.

The color former is characterized by forming a perceivable colorant product, e.g., black in color, representing a person's fingerprint when applied to the person's finger (or other parts of the body) and deposited onto a paper substrate in the presence of a developer. It is to be noted that when used herein the term fingerprint and fingerprint area includes a person's finger, palms, foot or other portion of the body, the print of which is unique to the individual.

The developer may be separate from the color former composition or an integral constituent thereof with a sufficient amount of chelating agent to inhibit the reaction between the color former and developer until the composition is applied to the fingerprint area and deposited onto a paper substrate. See my pending application Ser. No. 09/853,452 filed May 10, 2001, entitled Inkless Fingerprint Compound and Method, which application is incorporated herein by reference.

Alternatively, the developer may be included in the paper substrate as described in my U.S. Pat. No. 4,983,415 which patent is also incorporated herein by reference.

A third alternative for combining the color former with a developer at the time the fingerprint is to be taken is described in U.S. Pat. No. 4,182,261.

The developer, whether incorporated into the inkless composition or separately available as a coating on the paper substrate or in a separate reservoir to which the finger with the inkless composition thereon is to be subjected prior to the deposition of the print onto the paper substrate may be selected from one or more of the group of:

2,4,6-Trihydroxy Benzoic Acid
3,4,5-Trihydroxy Benzoic Acid
Dimethyl Glyoxime
Rubeanic Acid
Potassium Ferrocyanide
Sodium Ferrocyanide
Pyrogallol
Hydroxyquinoline and its derivatives e.g.,
quinolinol sulfate
Pyrocatechol
Propyl Gallate
Resorcinol
β-Resorcylic Acid
Tiron (4,5-Dihydroxy-m-Benzene Disulfonic acid Disodium Salt)
Gentisic Acid
Procatechuic Acid
Phloroglucinol
Tannic Acid
Sodium Tetrathionate
Sodium Thiosulfate
Diethyldithiocarbamic Acid
2-pyrrolidinecarbodithoic Acid A nonstaining ink which may be used in my invention is described in the '556 patent discussed earlier. The '556 patent is incorporated herein by reference. The nonstaining ink is formulated by dissolving one or more alcohol soluble dyes in one or more fatty acid esters which have at least one available hydroxyl group as described in detail in the '556 patent. It should be noted that the formulations described in that patent would need to be slightly modified to be in a semisolid state at ambient temperature by increasing the viscosity of the solvent. The dye preferably is a metal complexed dye, e.g., complexed with a polyvalent transition metal such as iron, chromium, copper or zinc. Three of the fatty acids may be glyceryl mononunoleate.

The following are several formulations of an inkless fingerprint composition (without developer) suitable for the present invention:

EXAMPLE 1

Combine polyoxyl 40 stearate (aka polyethylene glycol 400 stearate), ferric chloride hexahydrate, 2-phenoxyethanol (aka Dowanol EPH) as follows: 1000 grams PEG 400 stearate, 300 grams ferric chloride hexahydrate, and 100 grams 2-phenoxyethanol.

Polyoxyl 40 stearate has a congealing temperature of 37 to 47 degrees C.

EXAMPLE 2

1000 grams PEG 400 stearate, 300 grams ferric chloride hexahydrate, and 100 grams propylene glycol

EXAMPLE 3

1000 grams Lanolin, 300 grams ferric chloride hexahydrate, and 100 grams 2-phenoxyethanol.

It should be noted that the melting problem associated with a combination of lanolin and carbon based ink as used on the prior art foils is overcome in Example 3 formulation by the high solid concentration of ferric chloride hexahydrate. Also carbon based ink readily absorbs infrared energy thereby augmenting the problem of the lanolin melting. Ferric chloride hexahydrate does not have this problem.

A suitable formulation of an inkless fingerprint composition with a developer incorporated therein is as follows:
Polyethylene glycol 200 monolaurate-100 ml
Propylene glycol-300 ml
Polyethylene glycol 400 monostearate-700 g
Ferric chloride hexahydrate-90 g
Citric acid, anhydrous-65 g
8-Quinolinol-130 g

EXAMPLE 4 a nonstaining fingerprint composition for use in my invention may comprise: 850 grams PEG 400 monostearate, 150 grams of solvent, e.g., propylene glycol or 2-phenoxyethanol, solvent or oil soluble dye, e.g., 20 grams of nigrosine.

It should be noted that the above formulations are by way of examples only and are not to be considered as limiting the scope of the invention.

Figure 6:
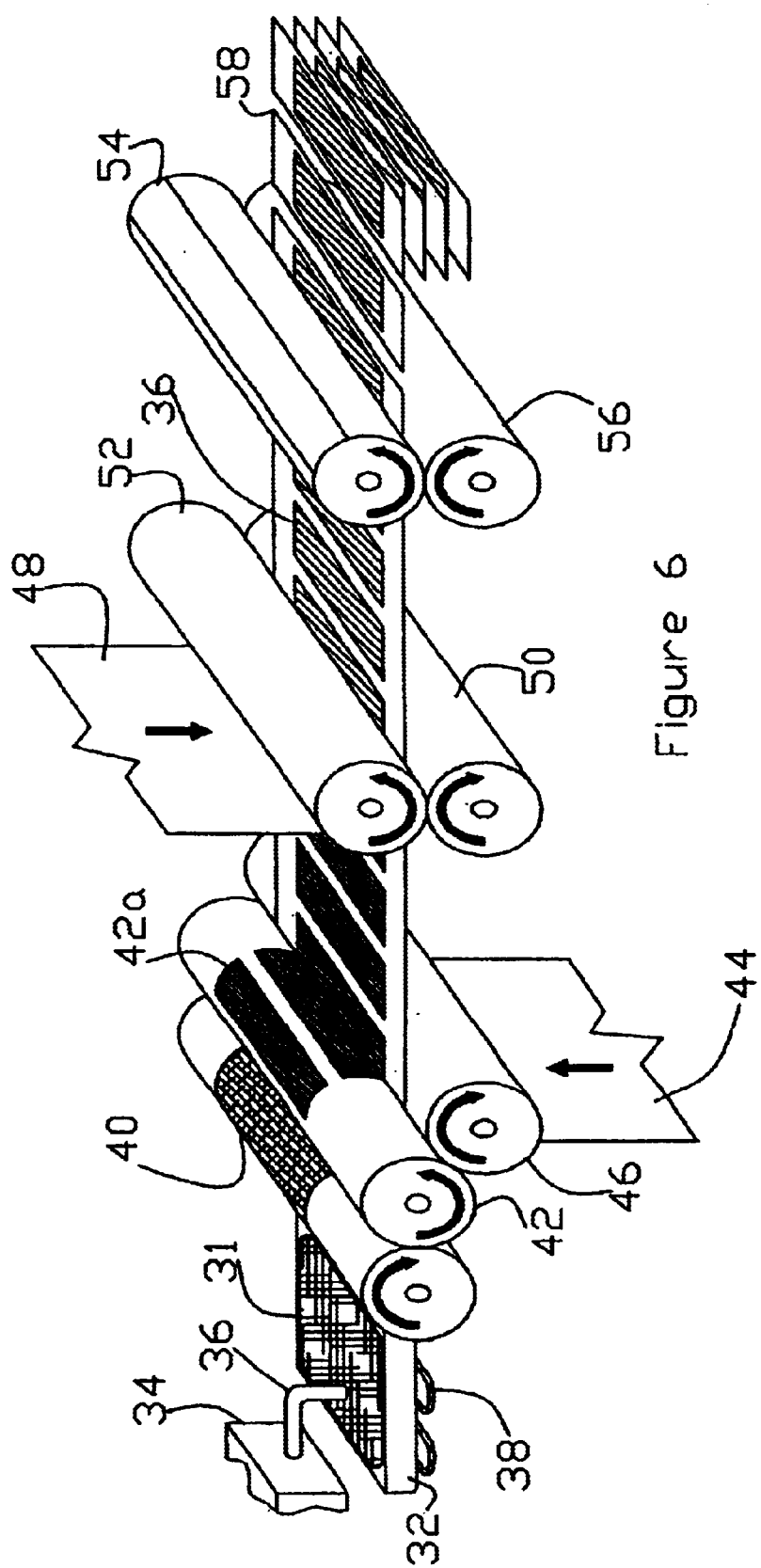
FIG. 6 is a diagrammatic perspective view of a simplified apparatus for making the disposable inkless fingerprint application of the present invention.

A method of manufacturing the disposable foil applicator with the inkless or nonstaining fingerprint composition contained therein is illustrated in FIG. 6.

The chosen composition 31 is dispensed into a tank or well 32 from a reservoir 34 via a dispensing nozzle 36. Heat from a suitable source such as an electric heater coil 38 heats the well 32 to maintain the inkless composition 31 in a liquid phase, i.e., at 110° F. or more. An offset roller 40 transfers the liquid composition to a printing roller 42 which has defined segregated rectangular areas 42a on the surface thereof which accept the composition and transfer it to a thin plastic sheet or film 44. The film may be Mylar having a thickness, for example, of about 0.001–0.005 inches and preferably about 0.002 inches. The film 44 is moved from a storage roll (not shown) under the printing roller 42 via a roller 46 and into contact with the composition on the surface areas 42a.

A second sheet of foil material 48, e.g., a 2 mil Mylar® plastic sheet, from a storage roll (not shown) is pressed over the top of the lower sheet 44 as the two sheets travel between rollers 50 and 52 to sandwich the inkless composition 31 in the form of separated rectangular layers between the two sheets as illustrated. A rotating cutter 54 in conjunction with a lower roller 56 cuts the sheets into individual rectangular sections each section 58 containing the inkless composition between the upper and lower foil strips. The superimposed strips 58 may then be cooled to room temperature, trimmed, if necessary, and packaged for subsequent shipment.

It should be noted that one of the sheets 44 or 48 is preferably made wider than the other to provide the staggard pull-tabs 26 and 28.

In use it is only necessary to separate the foil strips 20 and 22 by grasping the pull-tabs 26 and 28. One or both of the separated strips may then be used to apply the inkless composition thereon to the desired portion of the body to be fingerprinted, i.e., fingertip, palm, feet, etc.

There has thus been described a novel disposable applicator and inkless or nonstaining fingerprint composition which is inexpensive to manufacture, suitable for storage in relatively warm environments and easy to use without staining the fingers or other parts of the person being fingerprinted. Modifications of the preferred embodiment may be made without departing from the spirit and scope of my invention as defined in the appended claims.

What is claimed is:

1. A method of manufacturing an inkless fingerprint composition and disposable applicator therefore comprising:
   a) providing a first and second substantially nonpermeable foil strips, the strips have substantially the same width with the first strip being slightly longer than the second strip to provide an extended pull-tab when the strips are superimposed on one another;
   b) providing an inkless fingerprint composition which is semisolid at ambient temperature, the composition including a color former which when applied to a person's fingerprint area and deposited onto a proper substrate in the presence of a developer forms a permanent colorant product representing the person's fingerprint;
   c) evenly distributing a thin layer of the composition on a surface of one of the strips while leaving a border around the perimeter of the strip without the composition; and
   d) placing the other strip over said one strip so that the composition is sandwiched between the strips with a peripheral border of both strips and the peel tab area being unencumbered with the composition.

2. The method of claim 1 wherein the composition face border is about 1/16" in width.

3. The method of claim 1 wherein the inkless composition is heated to a liquid phase prior to distributing the composition onto the strip.

4. The method of claim 1 wherein the composition includes a nonstaining solvent compatible with the color former.

5. The method of claim 4 wherein the color former comprises one or more metal salts, where the metal of the metal salts is selected from the groups listed in the periodic table under columns 5A, 6A, 7A, 8A, 1B, 2B, 3B, 4B, 5B, and 7B.

6. The method of claim 5 wherein the metal of the metal salt is selected from one or more of the following transition metals: iron, titanium, vanadium, chromium, magnesium, cobalt, nickel, copper, zirconium, zinc, niobium, molybdenum, silver, tantalum and tungsten.

7. The method of claim 6 wherein the solvent in the inkless fingerprint composition comprises one or more reagents from the following group: glycol, glycol fatty acid esters, fatty acids, and fatty alcohols.

8. The method of claim 7 wherein the solvent is selected from one or more of the following group: glyceryl lanolate, glyceryl laurate, glyceryl myristate, glyceryl oleate/palmitate/ricinoleate, polyethylene glycol castor oils/cocoates/isosterates, polyethylene glycol lanolates, stearyl alcohol, myristyl alcohol, cetyl palmitate, cetyl alcohol and bees wax.

9. The method of claim 1 wherein the composition is in a liquid phase at a temperature of about 110° F. and above.

10. The method of claim 1 wherein the composition includes the developer and a sufficient amount of chelating agent capable of binding with the color former to substantially prevent the color former and developer from reacting in solution while permitting such reaction when the solution is applied to a person's fingerprint area and deposited onto a paper substrate.

11. The method of claim 10 wherein the developer is selected from one or more of the group of:
2,4,6-Trihydroxy Benzoic Acid
3,4,5-Trihydroxy Benzoic Acid
Dimemthyl Glyoxime
Rubeanic Acid
Potassium Ferrocyanide
Sodium Ferrocyanide
Pyrogallol
Hydroxyquinoline and its derivatives
Pyrocatechol
Propyl Gallate
Resorcinol
β-Resorcylic Acid
Tiron (4, 5-Dihydroxy-m-Benzene Disulfonic acid Disodium Salt)
Gentisic Acid
Procatechuic Acid
Phloroglucinol
Tannic Acid
Sodium Tetrathionate
Sodium Thiosulfate
Diethyldithiocarbamic Acid
2-pyrrolidinecarbodithoic Acid.

12. The method of claim 11 wherein the chelating agent is a carboxylic acid.

13. An inkless fingerprint composition and disposable applicator therefore comprising:
   a) first and second substantially nonpermeable foil strips, the strips have substantially the same width with the first strip being slightly longer than the second strip to provide an extended pull-tab when the strips are superimposed on one another; and
   b) a thin layer of an inkless fingerprint composition sandwiched between the superimposed strips leaving a small peripheral border and the pull-tab area free of the composition, the composition including a solution of a color former which is semisolid at ambient temperature, the color former being characterized by forming a perceivable colorant product representing a person's fingerprint when applied to the person's fingerprint area and deposited onto a paper substrate in the presence of a developer.

14. The invention of claim 13 where each of the foil strips comprise a plastic strip having a thickness within the range of about 0.001" to 0.005".

15. The method of claim 13 wherein the color former comprises one or more metal salts, where the metal of the metal salts is selected from the groups listed in the periodic table under columns 5A, 6A, 7A, 8A, 1B, 2B, 3B, 4B, 5B, and 7B.

16. The invention of claim 15 wherein the metals of the metal salts are selected from one or more of the following metals: iron, titanium, vanadium, chromium, magnesium, cobalt, nickel, copper, zirconium, zinc, niobium, molybdenum, silver, tantalum and tungsten.

17. The invention of claim 16 wherein the solvent of the inkless fingerprint composition comprises one or more reagents from the following group: glycol, glycol fatty acid esters, fatty acids, and fatty alcohols.

18. The invention of claim 17 wherein the solvent is selected from one or more of the following group: glyceryl lanolate, glyceryl myristate, glyceryl oleate/palmitate/ricinoleate, polyethylene glycol castor oils/cocoates/isosterates, polyethylene glycol lanolates, stearyl alcohol, myristyl alcohol, cetyl palmitate, cetyl alcohol and bees wax (a blend of fatty acid ester).

19. The invention of claim 13 wherein the composition is in a liquid phase at a temperature of about 110° F. and above.

20. The invention of claim 13 wherein the composition includes the developer and a sufficient amount of chelating agent capable of binding with the color former to substantially prevent the color former and developer from reacting in solution while permitting such reaction when the solution is applied to a person's fingerprint area and deposited onto a paper substrate.

21. The invention of claim 13 wherein the composition free border is about 1/16" in width.

* * * * *

UNITED STATES PATENT AND TRADEMARK OFFICE
CERTIFICATE OF CORRECTION

PATENT NO. : 6,749,919 B2
DATED : June 15, 2004
INVENTOR(S) : Arndt

It is certified that error appears in the above-identified patent and that said Letters Patent is hereby corrected as shown below:

Column 2,
Line 19, after "extended" insert -- pull-tab to allow a user to grasp both --.

Column 3,
Line 39, after "of" and before "transition" insert -- the --.

Column 8,
Line 12, delete "method" and insert -- invention --.

Signed and Sealed this

Twenty-third Day of November, 2004

JON W. DUDAS
*Director of the United States Patent and Trademark Office*